(12) United States Patent
Wang et al.

(10) Patent No.: US 11,320,375 B2
(45) Date of Patent: May 3, 2022

(54) MULTICOLOR FLUORESCENCE READER WITH DUAL EXCITATION CHANNELS

(71) Applicants: Yan Wang, San Diego, CA (US); Cory McCluskey, San Diego, CA (US)

(72) Inventors: Yan Wang, San Diego, CA (US); Cory McCluskey, San Diego, CA (US)

( * ) Notice: Subject to any disclaimer, the term of this patent is extended or adjusted under 35 U.S.C. 154(b) by 0 days.

(21) Appl. No.: 16/894,612

(22) Filed: Jun. 5, 2020

(65) Prior Publication Data

US 2021/0381980 A1 Dec. 9, 2021

(51) Int. Cl.
*C12Q 1/686* (2018.01)
*G01N 21/64* (2006.01)
*B01L 9/00* (2006.01)

(52) U.S. Cl.
CPC .......... *G01N 21/6428* (2013.01); *B01L 9/527* (2013.01); *C12Q 1/686* (2013.01); *G01N 2021/6441* (2013.01); *G06T 2207/10064* (2013.01)

(58) Field of Classification Search
CPC ....... G01N 21/6428; G01N 2021/6441; C12Q 1/686; B01L 9/528
See application file for complete search history.

(56) References Cited

U.S. PATENT DOCUMENTS

2013/0078663 A1*  3/2013  Herr ..................... G01N 33/561
                                                                 435/28
2015/0323462 A1*  11/2015  Ghosh ............. G01N 35/00029
                                                                 435/29

FOREIGN PATENT DOCUMENTS

CN       111157497 A    *   5/2020
JP         3828193 B2   *  10/2006   ............. G01N 21/64

* cited by examiner

*Primary Examiner* — David P Porta
*Assistant Examiner* — Fani Boosalis
(74) *Attorney, Agent, or Firm* — Lili Chen

(57) ABSTRACT

Provided is a fluorescence reader that uses two excitation channels and can read up to seven different fluorescent dyes in a single run. Each excitation channel has one light source and one single excitation filter and one dichroic mirror. One excitation channel is capable of exciting multiple fluorescent dyes and can be used to distinguish multiple dyes in combination with multiple emission filters. The excitation channels are driven by a motor that can automatically switch the two excitation channels for taking images of up to seven different fluorescent dyes. An algorithm to calibrate the crosstalk between different fluorescent dyes is also provided. Also provided is a method for analyzing digital PCR data using a ratio of two fluorescence emission readings.

17 Claims, 9 Drawing Sheets

MULTICOLOR FLUORESCENCE READER WITH DUAL EXCITATION CHANNELS

FIELD OF THE INVENTION

This invention relates to the field of fluorescence microscopy, especially relates to a multicolor fluorescence reader with dual excitation channel.

BACKGROUND OF THE INVENTION

Fluorescence microscopy is an essential tool in the field of life sciences that uses fluorescence to generate an image of a sample, which has endogenous or exogenous fluorophores, chemical compounds that can re-emit light upon light excitation. Its principle involves illuminating a sample with an excitation light of a specific wavelength bandwidth and detecting the emission light of a longer wavelength that is emitted from the sample irradiated by the excitation light. At the core of this technology is to use a set of filters to direct the excitation light to the sample and selectively let the emission light reach the detector while blocking the excitation light from doing the same. The set of filters include an excitation filter, a dichroic mirror, and an emission filter. During the fluorescence imaging, the source light passing through an excitation filter shines onto a dichroic mirror which reflects the excitation light to the sample. Upon illumination, the sample emits an emission light that passes through the dichroic mirror and an emission filter and is received by the detector. The excitation light cannot pass through the dichroic mirror or the emission filter, and is therefore blocked from reaching the detector. For a particular fluorescent dye, it usually has a set of an excitation filter, an emission filter and a dichroic mirror that optimally suits the physical property of the dye (e.g. the excitation and the emission spectra of the dye) and can generate images with the highest signal to noise ratio.

Multicolor fluorescence imaging has many applications, for example, visualization of subcellular structures and multiplexed digital PCR detection. The multicolor imaging techniques, when implemented successfully, can provide rich information about the subject of interest. However, there are challenges and limitations that hinders the wide application of this powerful technique. For multiple fluorescent dyes used in the multicolor imaging, multiple sets of filters are usually required to be installed in a microscope, leading to complicated and expensive machines that can be afforded only to a few lucky laboratories or institutes. It is also very difficult to find a group of dyes with manageable crosstalk among each other and to correct the crosstalk among multiple dyes. As a result, four-color fluorescence microscope is the most commonly found product on the market. It is hard to find a multicolor fluorescence microscope that can support more than five colors. There is a need to develop a simple and inexpensive fluorescence microscope that can support simultaneous imaging of more than five colors. The present invention satisfies this need and provides other benefits as well.

SUMMARY OF THE INVENTION

Provided is a multicolor fluorescence reader that uses two excitation channels and can read up to seven different fluorescent dyes in a single run. Each excitation channel has one light source and one single excitation filter and one dichroic mirror. One excitation channel is capable of exciting multiple fluorescent dyes and can be used to read multiple dyes in combination with multiple emission filters. The excitation channels are driven by a motor that can automatically switch the two excitation channels for taking images of up to seven different fluorescent dyes. An algorithm to calibrate the crosstalk between different fluorescent dyes is also provided.

In one embodiment of the invention, there provides a multicolor fluorescence reader, comprising an emission filter wheel and two excitation channels that can be automatically moved, wherein each excitation channel has a light source, an excitation filter, and a dichroic mirror, and wherein the multicolor fluorescence reader can read up to seven different fluorophores in a single run.

In some embodiments, the excitation channel is moved by a stepper motor via connecting gears.

In some embodiments, the emission filter wheel of the multicolor fluorescence reader has three, four, five, six or more emission filters. The emission filter wheel is driven by a stepper motor to switch different emission filters while taking images for different fluorescent dyes.

In some embodiments, the light source used in the multicolor fluorescence reader is selected from light-emitting diode (LED) lamps, xenon arc lamps and mercury-vapor lamps.

In some embodiments, the light source in a first excitation channel is a high-power LED lamp with a peak wavelength of <500 nm and the light source in a second excitation channel is a high-power LED lamp with a peak wavelength of >580 nm.

In some embodiments, the first excitation channel can be used to excite five different fluorophores and the second excitation channel can be used to excite two different fluorophores.

In some embodiments, the multicolor fluorescence reader is equipped with an emission filter wheel with six emission filters.

In some embodiments, the multicolor fluorescence reader has six emission filters that can be used to read seven fluorophores, for example, FAM, VIC, ABY, JUN, Cy5, Cy5.5 and ATTO.

In some embodiments, the multicolor fluorescence reader comprises a PCR chip holder that can hold multiple PCR chips.

In some embodiments, the multicolor fluorescence reader comprises a slide holder that can hold multiple glass slides.

In some embodiments, the crosstalk between two fluorophores can be corrected by a calibration constant which is empirically determined. The crosstalk between fluorophore A and B is corrected as follows:

$$F_A' = F_A - K_{B \to A} * F_B$$

$$F_B' = F_B - K_{A \to B} * F_A$$

Wherein $F_A$ and $F_B$ are raw fluorescence intensity of A and B, respectively; $F_A'$ and $F_B'$ are corrected fluorescence intensity of A and B, respectively; $K_{B \to A}$ is the calibration constant for correcting bleed-through from fluorescence channel B to A; and $K_{A \to B}$ is the calibration constant for correcting bleed-through from fluorescence channel A to B.

In some embodiments of the invention, there provides a method for correcting bleed-through from n different fluorescence channels into fluorescence channel A in multicolor fluorescence recordings, wherein corrected fluorescence intensity of fluorescence channel A is calculated as following:

$$F_A' = F_A - \Sigma_{i=1}^{n}(K_i * F_i)$$

wherein $F_A$ is raw fluorescence intensity of fluorescence channel A; $F_A'$ is corrected fluorescence intensity of fluorescence channel A; $K_i$ is calibration constant for correcting bleed-through from $i^{th}$ fluorescence channel to fluorescence channel A; $F_i$ is raw fluorescence intensity of $i^{th}$ fluorescence channel, and n is the number of different fluorescence channels that have bleed-through into fluorescence channel A, i is an integer from 1, 2, . . . to n, wherein the calibration constant $K_i$ for correcting bleed-through from a fluorescence channel to fluorescence channel A is empirically determined.

In some embodiments, it provides a the method for determining a calibration constant ($K_i$) for correcting bleed-through from $i^{th}$ fluorescence channel to fluorescence channel A comprises the steps of: a, obtaining a plurality of multicolor fluorescence recordings with the fluorescence intensity of fluorescence channel A ($F_A$) and the fluorescence intensity of $i^{th}$ fluorescence channel ($F_i$); b, displaying, on a scatter plot, adjusted fluorescence intensity of fluorescence channel A ($F_{Adj}$) and the fluorescence intensity of $i^{th}$ fluorescence channel ($F_i$), wherein $F_{Adj}=F_A-N_i*F_i$, wherein $N_i$ is a value that can be changed; c, varying $N_i$, in response to user input, and observing the change of the shape of the scatter plot of $F_{Adj}$ and $F_i$; and d, selecting the value of $N_i$ as the calibration constant ($K_i$) for correcting bleed-through from $i^{th}$ fluorescence channel to fluorescence channel A when the shape of the scatter plot is most close to flat status.

In one embodiment of the invention, it provides a method of analyzing digital PCR data, comprising: a, measuring a fluorescent emission in each micro-well of a dPCR chip before the start of a digital PCR ($F_s$); b, measuring a fluorescent emission in each micro-well of the dPCR chip at the end of the digital PCR ($F_e$); c, determining an emission ratio $T=F_e/F_s$ for each micro-well; d, using a threshold value for the emission ratio T to identify micro-wells with positive PCR amplifications; and e, calculating a percentage of positive PCR amplification as a result of the digital PCR.

In some embodiments, $F_s$ and $F_e$ are measurements of the same reporter fluorescent dye.

In some embodiments, $F_s$ is a measurement of a passive fluorescent dye and $F_e$ is a measurement of a reporter fluorescent dye.

DETAILED DESCRIPTION

Figure 1:
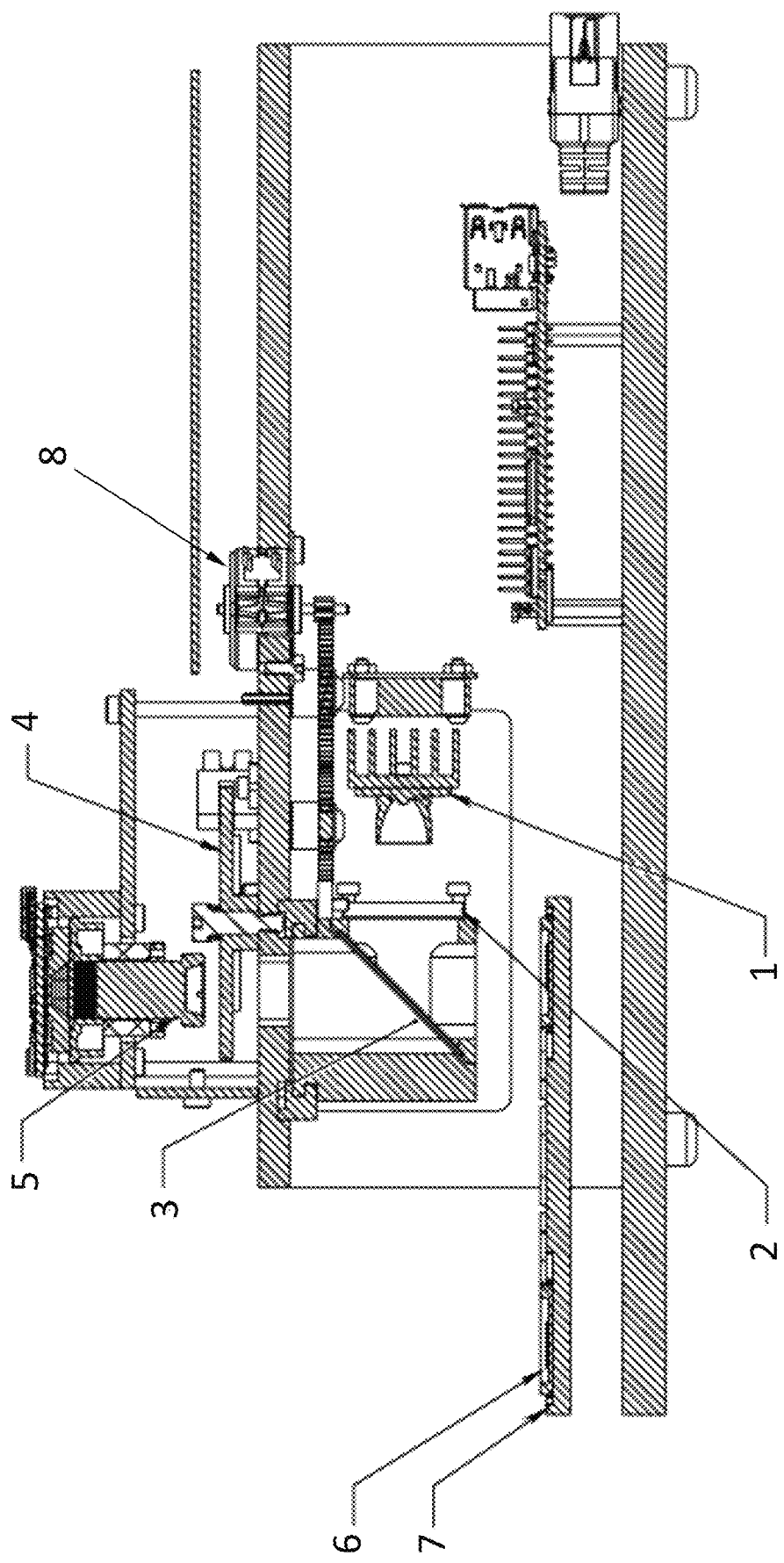
FIG. 1 is a side section view of a fluorescence microscope embodiment of the invention showing the major components, including dual excitation channel having two LED light sources (1), two emission filters (2) and two dichroic mirrors (3), an emission filter wheel (4), a camera (5), PCR chips (6), a PCR chip holder (7) and a controlling motor for the excitation channels (8).

Abbreviations: DNA—deoxyribonucleic acid; RNA—Ribonucleic acid; and PCR—polymerase chain reaction.

Definitions: Unless otherwise defined, all technical and scientific terms used herein have the same meaning as commonly understood by one of the ordinary skill in the art to which this invention belongs.

The term "a" and "an" and "the" as used to describe the invention, should be construed to cover both the singular and the plural, unless explicitly indicated otherwise or clearly contradicted by context. Similarly, plural terms as used to describe the invention, should also be construed to cover both the plural and the singular, unless indicated otherwise or clearly contradicted by context.

The term "excitation channel", as used herein, refers to a set of optical components in a fluorescence reader that are used to send an excitation light of specific bandwidth to a sample to be tested. An excitation channel usually includes a light source, an excitation filter and a dichroic mirror. There may be multiple light sources, excitation filters and dichroic mirrors in one excitation channel. The excitation channel of the invention has a single light source, a single excitation filter and a single dichroic mirror.

Majority of the optical systems commonly used for fluorescent microscopy requires expensive filter sets to allow simultaneous detection of multiple fluorescent dyes. Each filter set has an excitation filter, an emission filter and a dichroic mirror optimized for the excitation and emission spectra of a single fluorophore. Multicolor fluorescent imaging is limited by the number of the filter sets that can be accommodated by the microscope. High number of filter sets also significantly increases the cost of the microscope. Some system uses laser of different wavelengths to excite different fluorophores. The number of colors that can be measured is limited to the availability of lasers and the compatibility of different fluorescent dyes. Increase of the number of lasers increases the complexity of the microscope and also contributes to the increase of the instrument cost. This is why the most common multicolor fluorescent imaging is less than four colors. The fluorescence microscope that can image more than 5 colors is very rare to find.

In one embodiment of the invention, it provides a fluorescence reader using two excitation channels in combination of emission filters to read up to seven fluorophores. Each excitation channel includes a light source, an excitation filter and a dichroic filter. One excitation channel produces an excitation light of a shorter wavelength (e.g. <500 nm) that can be used to excite five categories of commonly used fluorescent dyes such as FAM, VIC, ABY, ATTO and JUN. Another excitation channel produces an excitation light of a longer wavelength (e.g. >600 nm) that can be used to excite fluorescent dyes with longer excitation wavelength such as Cy5.5 and Cy5. The fluorescent dyes excited by the same excitation channel is distinguished by different emission filters. This setup can provide excitation lights of both shorter and longer wavelengths without extensive use of excitation filters. It provides a simple and easy to operate alternatively to the currently available models. It can easily measure up to seven different fluorescent dyes with only a portion of the cost.

Figure 2:
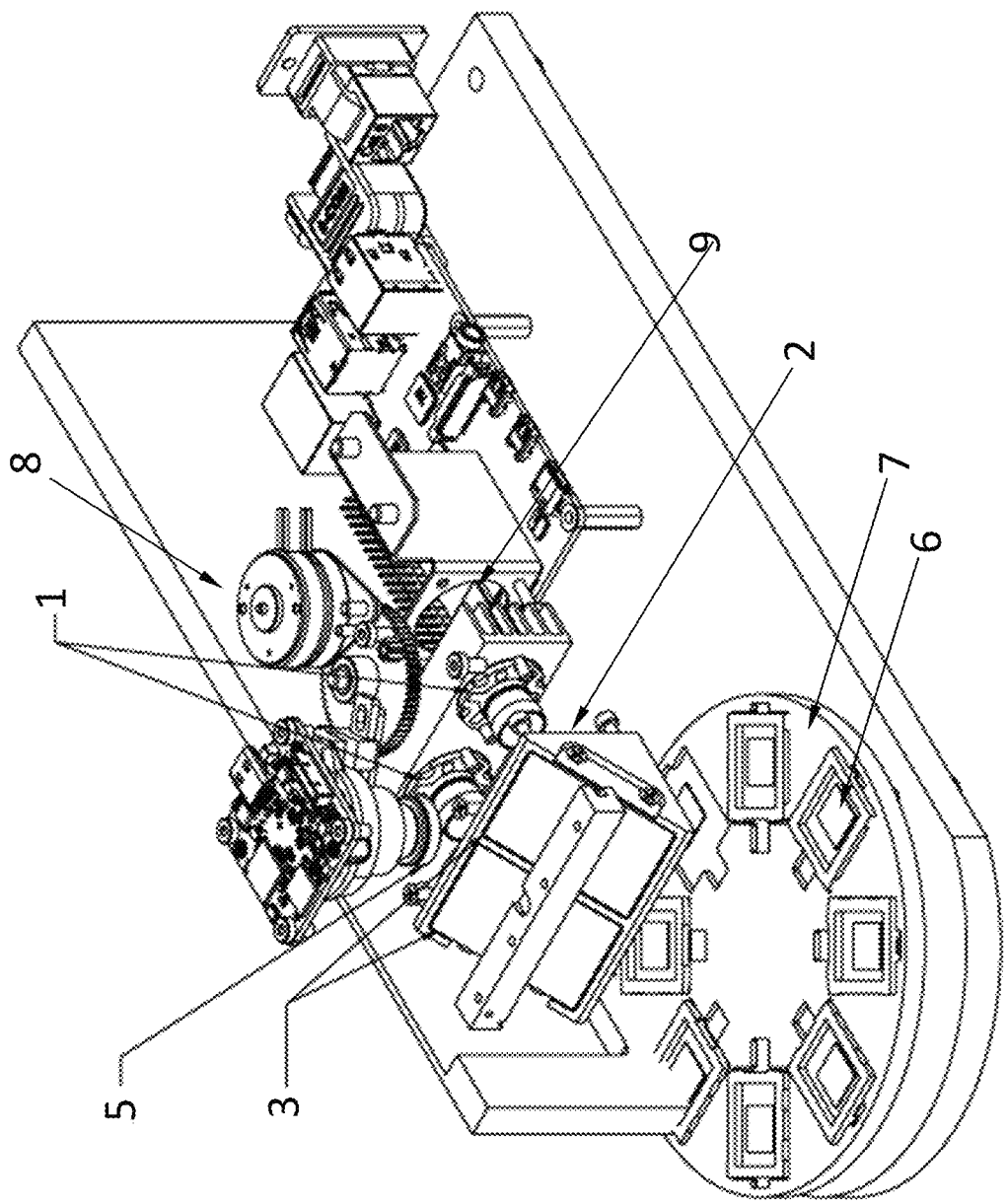
FIG. 2 is an inside view of the fluorescence microscope showing the positioning of two LED light sources (1) and two excitation filters (2), two dichroic mirrors (3), a camera (5), PCR chips (6), a PCR chip holder (7), a controlling motor for the excitation channels (8), and a holding track for the excitation channels (9).
Figure 3:
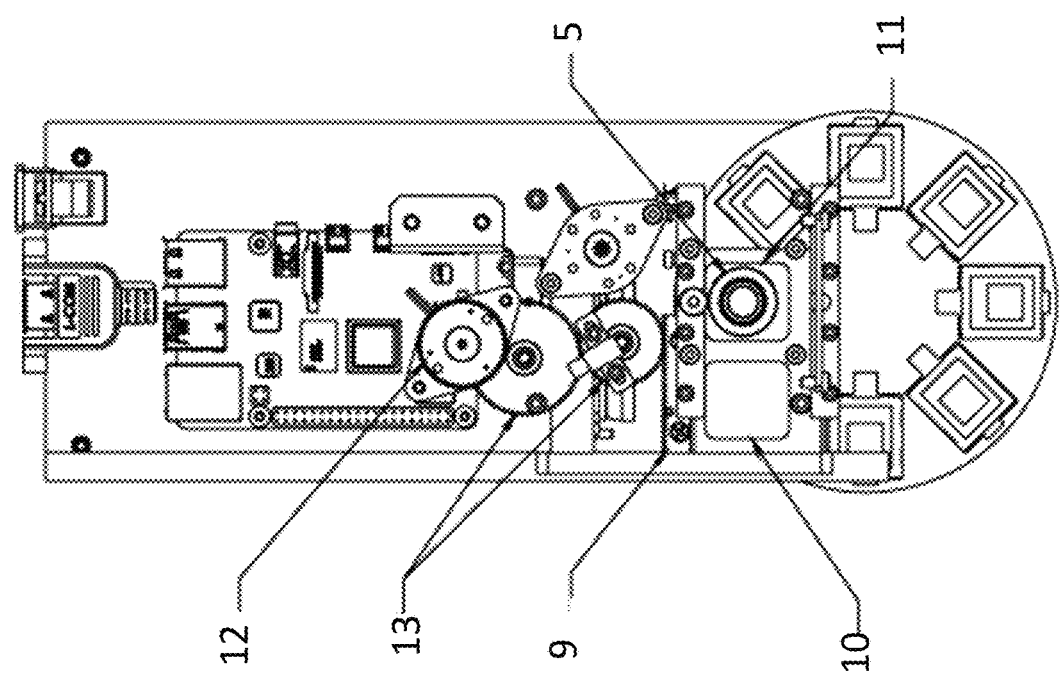
FIG. 3 is a top view of the machine showing the first excitation channel (10), the second excitation channel (11), a stepper motor for moving the excitation channel (12), gears turned by the stepper motor to move the excitation channel (13), and a holding track along which the two excitation channels can be moved (9).

In one embodiment of the invention, it provides a multi-color fluorescence reader that can read up to seven different fluorophores in a single run, comprising an emission filter wheel and two excitation channels that can be automatically moved, wherein each excitation channel has a light source, an excitation filter, and a dichroic mirror. As shown in FIGS. 1-3, the two excitation channels (10&11) are placed side by side underneath the camera (5). Samples are placed below the excitation channels and the emission filter wheel (4) is positioned between the camera (5) and the excitation channels (10&11). Samples used in the fluorescence reader can be, for example, digital PCR chips, microarrays slides, cell staining slides, etc. In some embodiments, the fluorescence reader is equipped with a digital PCR chip holder, which could hold, for example, 3, 4, 5, 6, 7, 8, 9, 10, 11, 12 or more PCR chips. In some embodiments, the fluorescence reader is equipped with a glass slide holder, which could hold, for example, 1, 2, 3 or 4 glass slides. Each excitation channel packed as one unit has a single light source (1), a single excitation filter (2), and a dichroic mirror (3), which can be moved along a holding track (9) by a controlling motor (8). The controlling motor (8) comprises a stepper motor (12) and connecting gears (13) driven by the stepper motor (12). The controlling motor can be programmed to move one of the two excitation channels to be directly underneath the camera for picture taking. During the imaging process, the light source sends out a light beam that is filtered by the excitation filter. The pass-through light, the excitation light, is reflected by the dichroic mirror to shine onto the sample. Upon illumination by the excitation light, the sample emits an emission light of longer wavelength that can pass through the dichroic mirror. The emission light is further filtered by a selected emission filter and the pass-through emission light will be detected by the camera. Both the dichroic mirror and the emission filter are used to block the excitation light and prevent it from reaching the camera.

The first excitation channel can generate an excitation light with shorter wavelength and the second excitation channel can generate an excitation light with longer wavelength so that a wide spectrum of fluorescent dyes can be excited using both excitation channels. For example, the first excitation channel can use a blue LED lamp with a peak wavelength shorter than 500 nm (e.g. 460 nm, 465 nm, 470 nm, 475 nm, 480 nm, or 490 nm) to excite commonly used fluorescent dyes such as FAM, VIC, ABY, ATTO and JUN. An excitation filter with a band pass of 20 nm, 30 nm, 40 nm, 50 nm or 60 nm can be used to filter the LED excitation light. A dichroic mirror selected should be able to reflect the excitation light with a wavelength of, for example, 430-490 nm, 440-500 nm, 450-520 nm, or 420 nm-500 nm, and pass through emission lights of the fluorescent dyes used. The lights emitted from the fluorescent dyes are further filtered by respective emission filters on the emission filter wheel.

The second excitation channel can use a red LED lamp with a peak wavelength longer than 580 nm (e.g. 580 nm, 610 nm, 615 nm, 617 nm, or 620 nm) to excite fluorescent dyes that can be excited by long wavelength lights such as Cy5.5 and Cy 5. An excitation filter of an appropriate band pass is used to filter the LED excitation light. The excitation filter is chosen to pass through an excitation light that can efficiently excite the fluorescent dyes of choice and have no overlap with the bandwidth of the emission lights of the fluorescent dyes. The wavelength band pass of the excitation filter can be, for example, 575-620 nm, 590-640 nm or 585-635 nm. The dichroic mirror selected for the second channel should be able to deflect long wavelength excitation light having a deflection range of, for example, 500-630 nm, 400-620 nm, or 450-625 nm. The pass-through wavelength range of the dichroic mirror is selected depending on the emission wavelengths of the fluorescent dyes.

Figure 4:
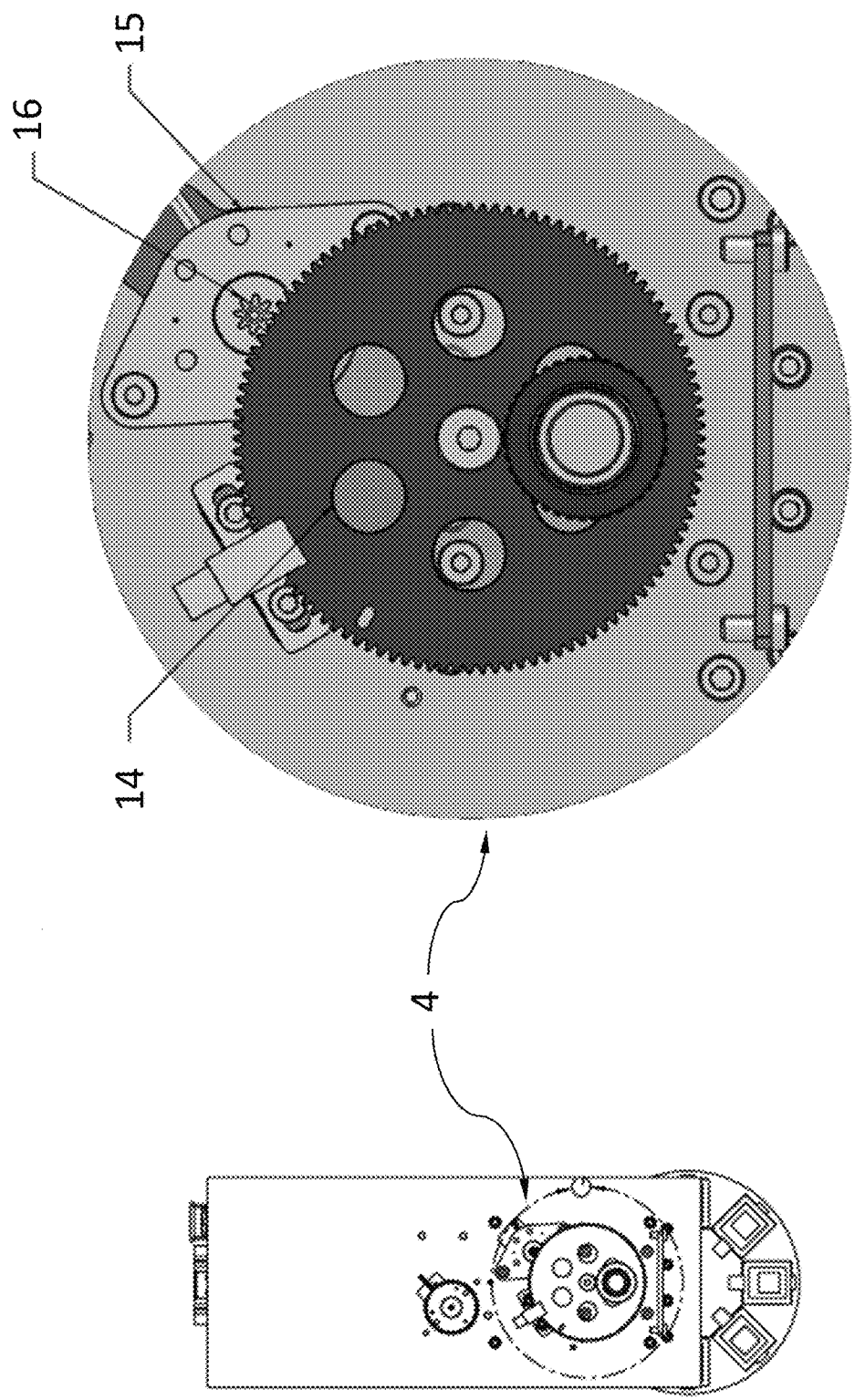
FIG. 4 is a top view of an emission filter wheel (4) that has six emission filters (14) driven by a stepper motor (15) using a connecting pinion (16).

FIG. 4. shows a top view of the emission filter wheel (4) that comprises six emission filters (14), which can be rotated by a motor to select the correct emission filter for a particular fluorescent dye. The motor for rotating the emission filter wheel comprises a stepper motor (15) and connecting pinion (16). The stepper motor moves the connection pinion, which in turn moves the emission filter wheel. The emission filter wheel may contain 4, 5, 6, 7, 8 or more emission filters. Since multiple fluorescent dyes are excited by the same excitation channel, they can be distinguished by narrow-banded emission filters.

An emission filter for a fluorescent dye is usually set around the peak wavelength of an emission light. It can also be set at a wavelength range apart from the peak wavelength in order to separate two fluorescent dyes with close emission spectra. The bandwidth of an emission filter can be, for example, 10 nm, 15 nm, 20 nm, 25 nm, 35 nm or 40 nm. For fluorescent dyes having close emission spectra, the bandwidths of emission filters need to be set to a narrower range (e.g. 8 nm or 10 nm) so that the emission lights for the two fluorescent dyes can be distinguished. If two neighboring fluorescent dyes have wide spread emission spectra, the bandwidth of emission filter chosen can have a wider range, for example, 35 nm or 40 nm.

Sometimes, two fluorescent dyes can share the same emission filter because they are excited at different wavelengths. For example, ATTO and Cy5 can be excited by the first and second excitation channel, respectively. The ATTO and Cy5 have emission lights with peak wavelengths at 658 nm and 676 nm, respectively, which can share an emission filter that covers the peak wavelength for both fluorescent dyes. This setting allows using six emission filters and two excitation channels to separately measure seven different dyes. The seven fluorescent dyes are measured sequentially, and the imaging data can be combined in the analysis afterwards. The crosstalk between multiple fluorescent dyes can be corrected by a calibration constant, which is determined empirically.

Figure 5:
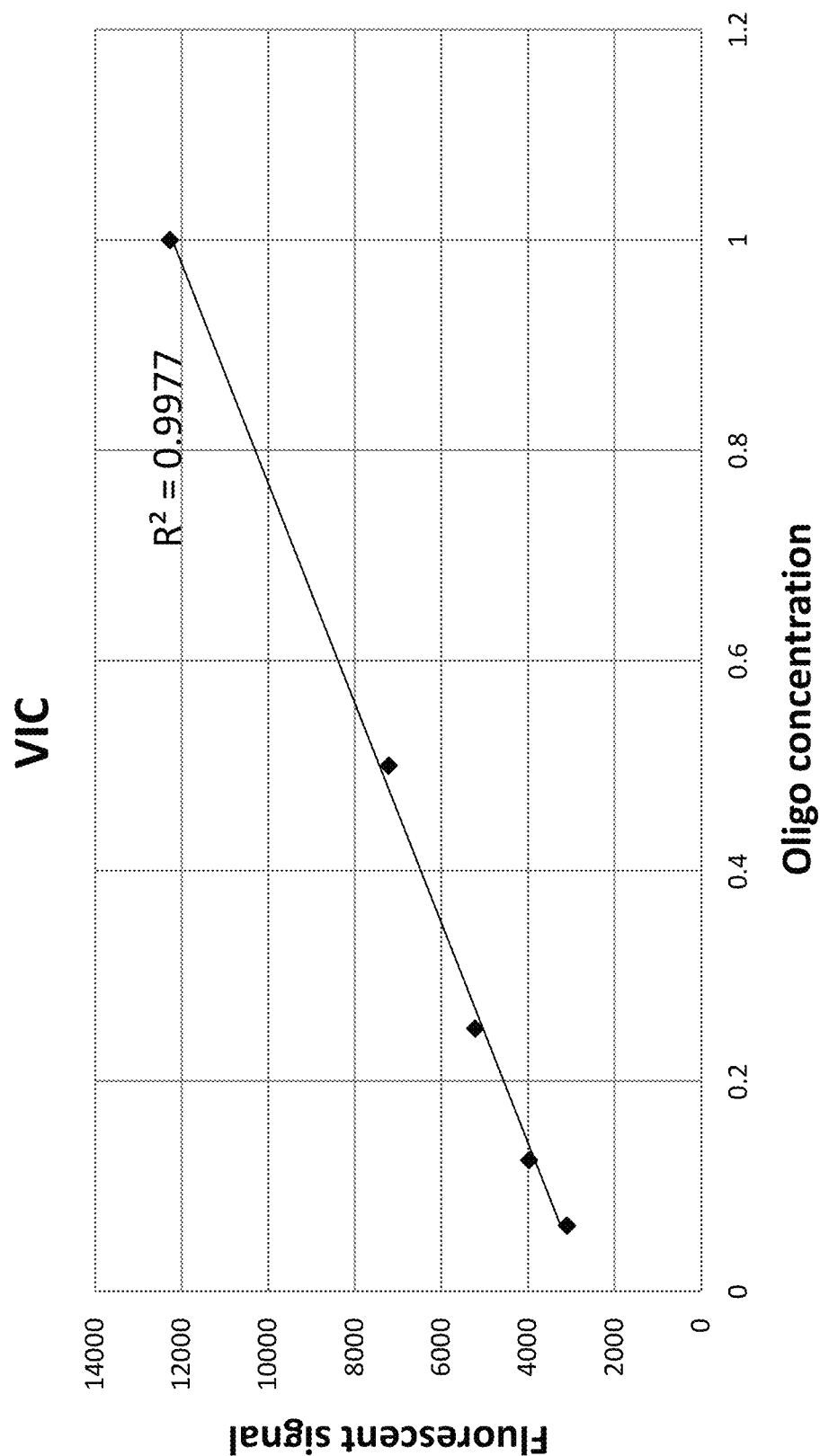
FIG. 5 shows a linearity analysis of the concentration of a fluorescence dye (VIC) and the measured fluorescence intensity. The x-axis and y-axis represent the concentration of VIC-labeled oligo nucleotide and the fluorescence intensity, respectively.
Figure 6:
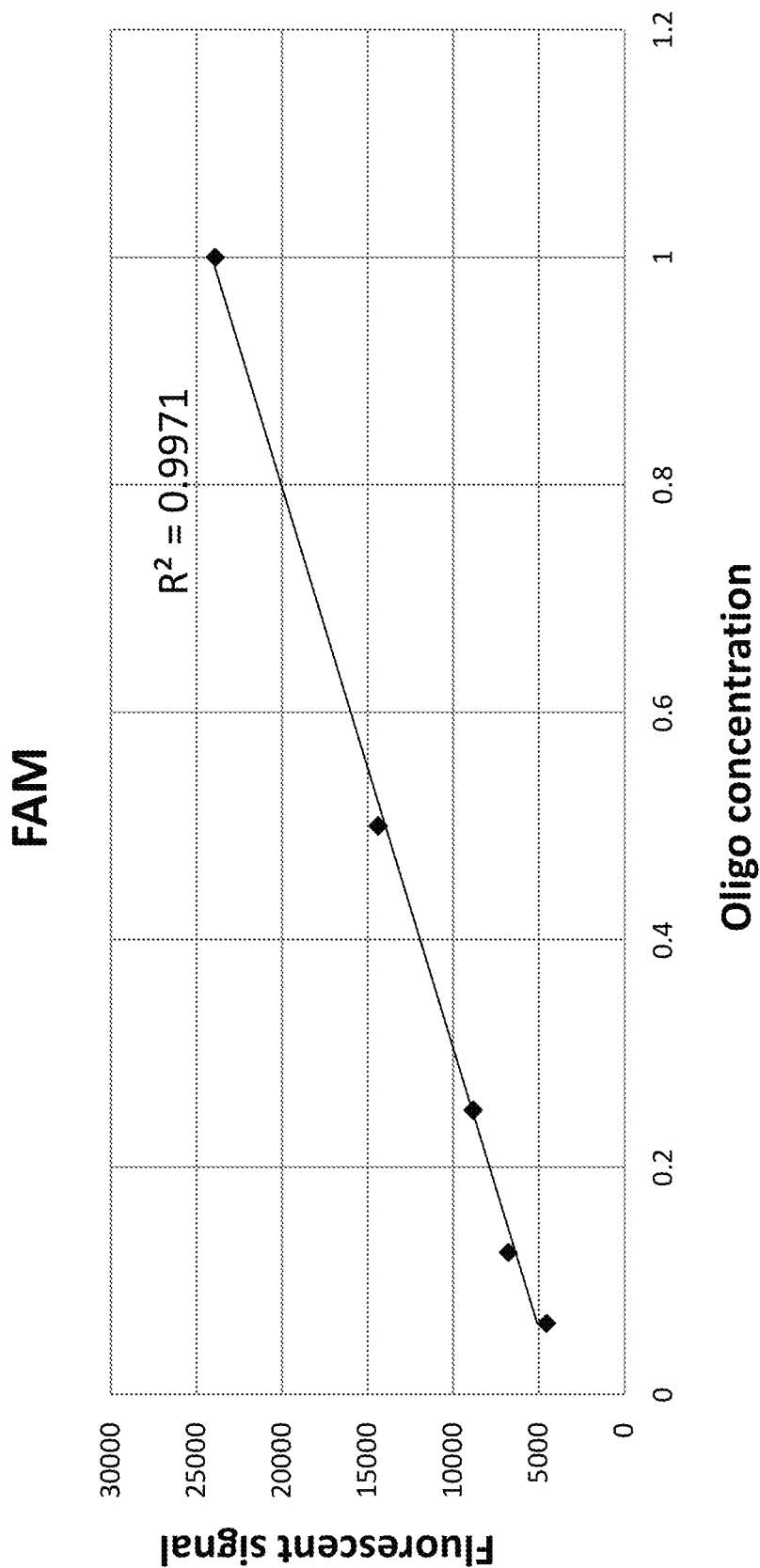
FIG. 6 shows a linearity analysis of the concentration of a fluorescence dye (FAM) and the measured fluorescence intensity. The x-axis and y-axis represent the concentration of FAM-labeled oligo nucleotide and the fluorescence intensity, respectively.

FIGS. 5 and 6 show linearity analysis of two fluorescent dyes, FAM and VIC. It was tested to see if the measured fluorescence intensity and the concentration of fluorescent dye has a good linear relationship. Different concentrations of oligonucleotides labeled with a single fluorescent dye were measured in the fluorescence reader, and the concentration of the dye is plotted against the measured fluorescence intensity. The results show that the concentrations of both fluorescent dyes have very good linear relationship with the fluorescence measurement. The coefficient of determination ($R^2$) of both dyes are higher than 0.99, indicating a very good linear relationship. The same experiments were also done for other five fluorescent dyes. All of them have good linearity with $R^2$ values higher than 0.99. These results indicate that the concentration of the fluorescent dye and the measured fluorescence has a very good linear relationship.

Figure 7:
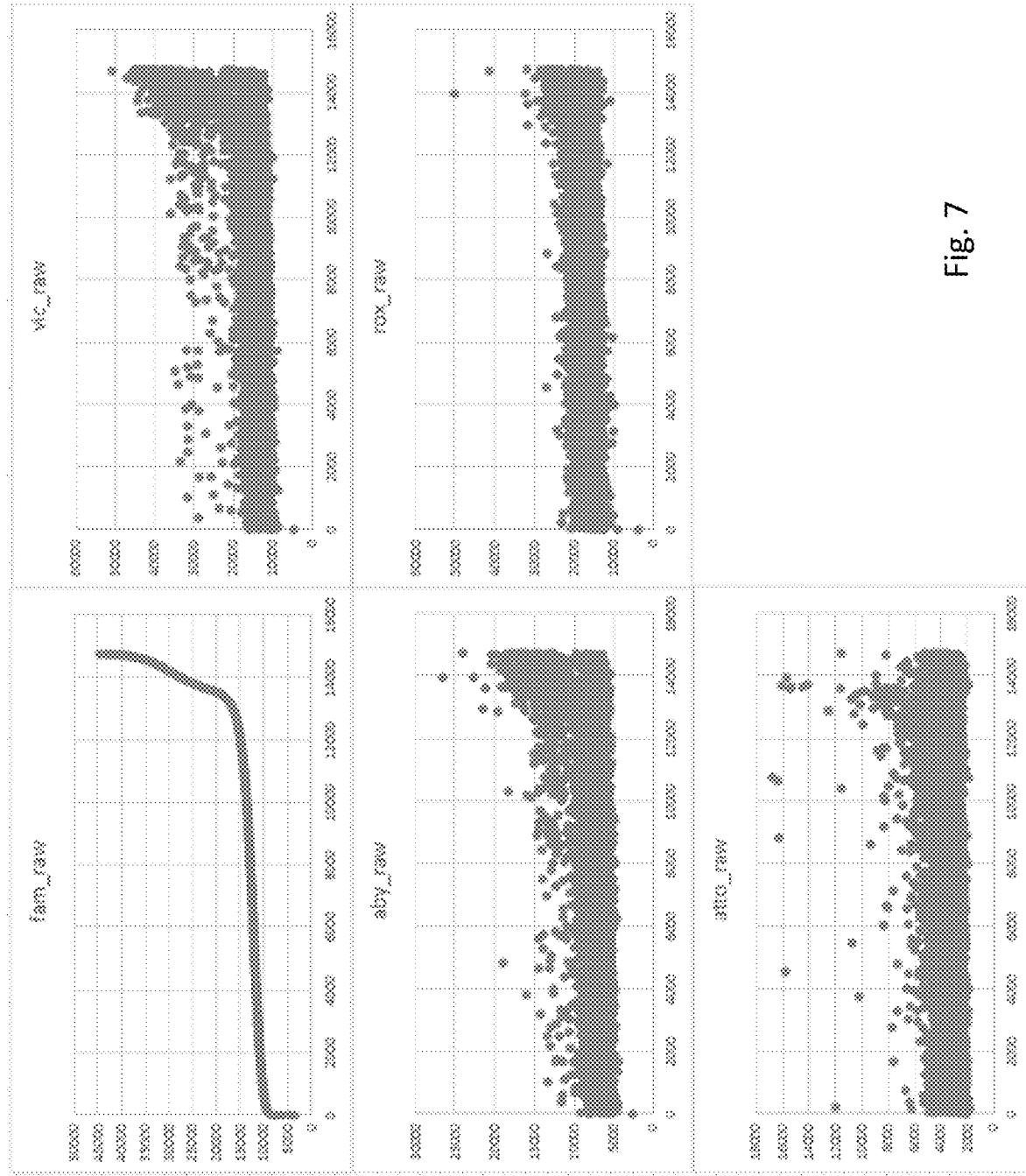
FIG. 7 shows a test result of how fluorescent dye FAM affects measurement readings of other fluorescent dyes including VIC, ABY, ROX and ATTO.

When multiple fluorescent dyes are measured, it is important to test whether the signal of a fluorescent dye is bled through into the signal of another and make correction of the crosstalk. FIG. 7 shows the result of a method for testing if the signal of fluorescent dye is bled through into other fluorescent channels. The method tests if the increase of signals of a single fluorescent dye can lead to increase of signals in another fluorescent channel. If the answer is yes, it indicates that the fluorescent dye of the test may bleed through into another fluorescent dye, and calibration of the signal bleed-through needs to be done. If the answer is no, it indicates that the increase of the fluorescent dye of the test does not have any effect on the other fluorescent dye, and it is likely that the tested fluorescent dye does not bleed through into the channel of other dye.

Figure 8:
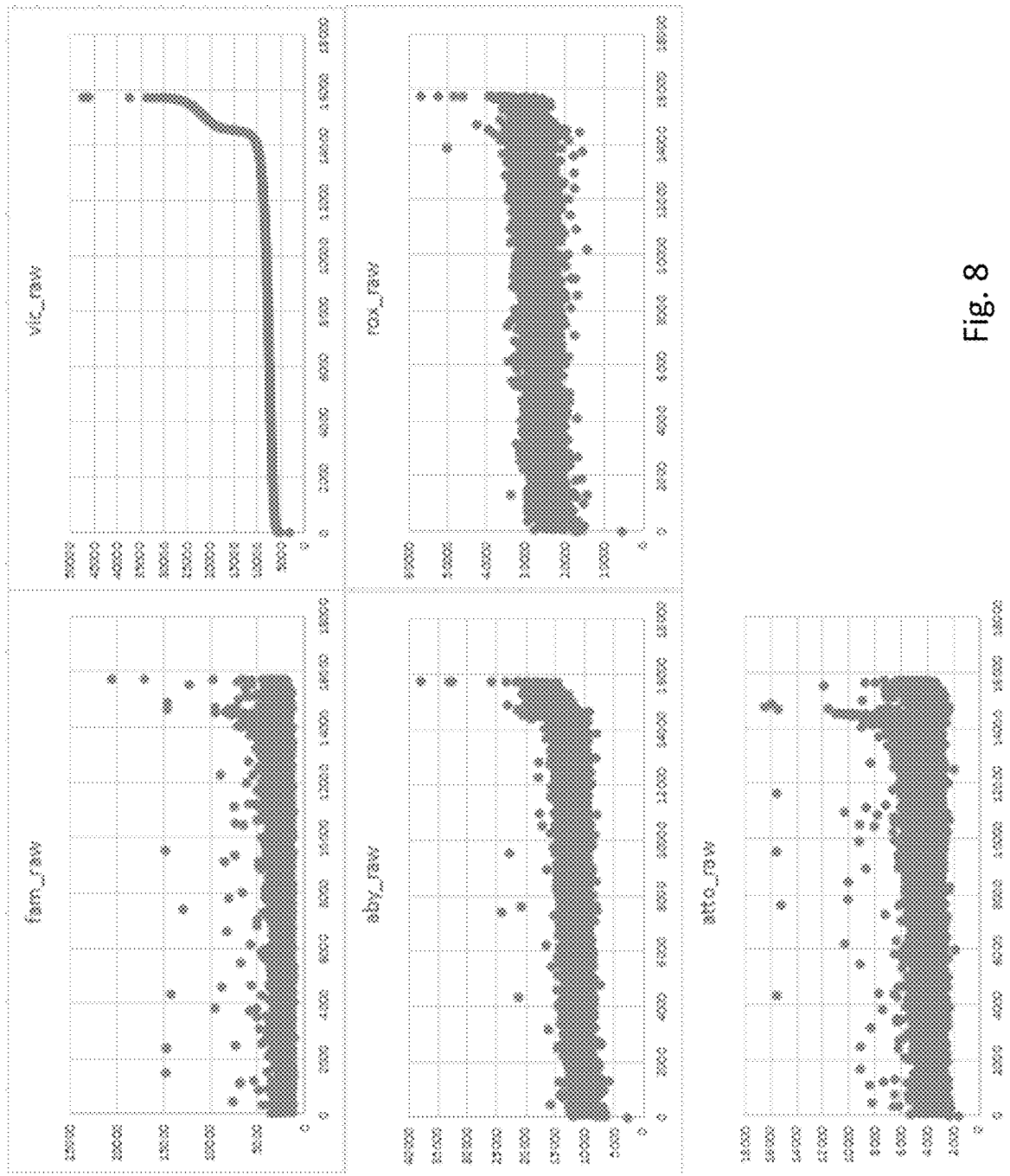
FIG. 8 shows a test result of how fluorescent dye VIC affects measurement readings of other fluorescent dyes including FAM, ABY, ROX and ATTO.

A digital PCR experiments was performed in a digital PCR chip using only one single fluorescent labeling of FAM. The fluorescent reader read the fluorescence intensity for FAM, VIC, ABY, ROX and ATTO in 20,000 wells of the digital PCR chip. There is no VIC, ABY, ROX or ATTO in the wells of the digital PCR chip. If there is no bleed-through from FAM to other fluorescence channel, the readings in VIC, ABY, ROX and ATTO channel should show only background noise. On the other hand, if there is bleed-through from FAM to another fluorescence channel, the affected channel will have higher readings with increase of FAM signals. The measured FAM intensity of all the wells were sorted from lowest (left) to highest (right). The corresponding intensity readings of the aligned wells for all the fluorescent dyes were plotted in FIG. 7. When the measured FAM intensity was increased, the fluorescent intensity readings in the corresponding wells for ROX and ATTO did not have significant change while the fluorescent intensity readings for VIC and ABY were significantly increased with the increase of FAM fluorescence readings. These results indicate that FAM signals do not bleed into the fluorescence channel of ROX and ATTO, and FAM signals do bleed into the fluorescence channel of VIC and ABY. The same experiments were performed for other fluorescent dyes as well. FIG. 8 shows another example of testing if VIC fluorescence signals bleed into other fluorescence channels. The results indicate that VIC fluorescence signals may have small bleed-through into the fluorescence channel of ATTO, but not into fluorescence channels of other dyes.

The crosstalk calibration among multiple fluorescent dyes should be done in a stepwise manner. The first step is to determine if two fluorescent dyes have crosstalk. The second step is to first calibrate the crosstalk between two fluorescent dyes that have the closest emission spectra, and then calibrate with the dye with the next closest emission spectra, until all the crosstalk is corrected. Usually, the raw fluorescence intensity readings are corrected for factors such as light evenness, shape of the well, physical artifacts before the crosstalk calibration. For example, the raw fluorescence intensity readings can be corrected by dividing the raw value with a reference value, if available. For digital PCR experiment, a reference dye, ROX, are evenly added to all the wells in a digital chip. The ROX reading can then be used as the reference value.

The key for calibrating crosstalk between two fluorescent dyes is to find a calibration constant for bleed-through from one dye to another. Once the calibration constant is determined, the crosstalk between fluorophore A and B is corrected as follows:

$$F_A' = F_A - K_{B \to A} * F_B \qquad (a)$$

$$F_B' = F_B - K_{A \to B} * F_A \qquad (b)$$

wherein $F_A$ and $F_B$ are raw fluorescence intensity of A and B, respectively; $F_A'$ and $F_B'$ are corrected fluorescence intensity of A and B, respectively; $K_{B \to A}$ is the calibration constant for correcting bleed-through from fluorescence channel B to A; and $K_{A \to B}$ is the calibration constant for correcting bleed-through from fluorescence channel A to B. The calibration constant is determined empirically. For example, if a fluorescence channel A is bled into the fluorescence channel of B, the plot of readings of fluorescence dye A vs. readings of fluorescent dye B will have a linear relationship with a slop bigger than 0. The bigger the slope, the more bleed-through from the fluorescence channel A into B. To correct for the bleed-through of A into B, different calibration constants from 0 to 1 can be tested in the equation (b) to obtain corrected $F_B'$. Plot the $F_A$ vs. the corrected $F_B'$ to obtain a slope of the linear relationship. The correct final calibration constant ($K_{A \to B}$) should make the slope of the above plot be closest to 0. The intensity value corrected for A to B bleed-through will be $F_B' = F_B - K_{A \to B} * F_A$. Sequentially correct the bleed-through from fluorescence channel of other fluorescent dyes (e.g. C, D), and the corrected final value for fluorescent dye B will be determined, that is, $$F_B' = F_B - K_{A \to B} * F_A - K_{C \to B} * F_C - K_{D \to B} * F_D$$

The same calibration procedure should be applied to every fluorescent dye to obtain the corrected value for each dye.

In some embodiments, there provides a method for correcting bleed-through from n different fluorescence channels into fluorescence channel A in multicolor fluorescence recordings, wherein corrected fluorescence intensity of fluorescence channel A is calculated as following:

$$F_A' = F_A - \Sigma_{i=1}^{n}(K_i * F_i)$$

wherein $F_A$ is raw fluorescence intensity of fluorescence channel A; $F_A'$ is corrected fluorescence intensity of fluorescence channel A; $K_i$ is calibration constant for correcting bleed-through from $i^{th}$ fluorescence channel to fluorescence channel A; $F_i$ is raw fluorescence intensity of $i^{th}$ fluorescence channel, and n is the number of different fluorescence channels that have bleed-through into fluorescence channel A, wherein the calibration constant for correcting bleed-through from a fluorescence channel to fluorescence channel A is empirically determined.

In some embodiments, a method is provided for determining a calibration constant ($K_i$) for correcting bleed-through from $i^{th}$ fluorescence channel to fluorescence channel A. The method comprises the steps of: a, obtaining a plurality of multicolor fluorescence recordings with the fluorescence intensity of fluorescence channel A ($F_A$) and the fluorescence intensity of $i^{th}$ fluorescence channel ($F_i$); b, displaying, on a scatter plot, adjusted fluorescence intensity of fluorescence channel A ($F_{Adj}$) and the fluorescence intensity of $i^{th}$ fluorescence channel ($F_i$) of the plurality of multicolor fluorescence recordings, wherein $F_{Adj} = F_A - N_i * F_i$, wherein $N_i$ is a variable that can be changed; c, varying $N_i$, in response to user input, and observing the change of the shape of the scatter plot of $F_{Adj}$ vs. $F_i$; and d, selecting the value of $N_i$ as the calibration constant ($K_i$) for correcting bleed-through from $i^{th}$ fluorescence channel to fluorescence channel A when the shape of the scatter plot is most close to flat status.

The method can be implemented either manually or by a computer-based program. For manual implementation, one can change $N_i$ from 0 to a positive value in a stepwise manner. For each selected $N_i$, make a scatter plot of $F_{adj}$ vs. $F_i$ of a plurality of multicolor fluorescence recordings. If there is bleed-through from fluorescence channel i into fluorescence channel A, the intensity in fluorescence channel A is increased with the increase of intensity in fluorescence channel i. In a scatter plot of the two fluorescence intensities, the shape of scattered dots is slanted upwards, indicative of positive correlation between the two fluorescence intensities. Find an $N_i$ for adjusting the $F_A$ such that the correlation between the two fluorescence intensities ($F_{adj}$ and $F_i$) is at the minimum level. In a scatter plot of the adjusted fluorescence intensity $F_{adj}$ vs. $F_i$, the shape of scattered dots should be at minimum slanted upwards, ideally, be at a flat status. When such an $N_i$ is found, it is selected as the calibration constant $K_i$ for correcting the bleed-through from the fluorescence channel i to the fluorescence channel A. The method can be repeated until all the calibration constants are determined for any two fluorescence channels with crosstalk.

The method can also be implemented by a computer program. The computer program provides a graphic user interface for user to choose any two fluorescence channels ($F_A$ and $F_i$) to perform crosstalk calibration. It provides a functional bar for changing the value of $N_i$ along with a display of the corresponding scatter plot of the two selected fluorescence channels ($F_{adj}$ and $F_i$). When a user changes the value of $N_i$, the change of fluorescence intensities ($F_{Adj}=F_A-N_i*F_i$) is directly reflected in the companying scatter plot, which enables the user to select an appropriate $N_i$ as the calibration constant based on the change of the shape of the scattered dots in the scatter plot. The program allows a user to adjust $N_i$ while visually inspecting the change of adjusted data so that the user can easily find an appropriate calibration constant for two channels with crosstalk.

A chip-based digital PCR is carried out by partitioning a sample into a large number of micro-wells of a digital PCR chip to perform a large number of PCR microreactions in parallel. The positive amplification is determined at the end of the digital PCR by detecting fluorescent chemicals generated during PCR amplifications in the micro-wells. This is called an end-point digital PCR where only one measurement is done at the end of the reaction. The end-point fluorescent emission readings are compared to a threshold and those with end-point fluorescent emission readings higher than the threshold are determined to have positive amplifications. Since this method uses only one measurement to determine positive/negative outcomes, variation factors among different micro-wells, including volume variations, differences in position and shape, and fluorescent dye concentration variations, can contribute to variations in the final result, leading to high incidences of false positives and false negatives. To minimize and compensate for the effects of these variation factors, a method is provided to measure fluorescent emissions before and after a digital PCR and use the ratio of the two fluorescent emission readings as the determinant for detecting positive/negative amplifications.

In one embodiment of the invention, there provides a method of analyzing digital PCR data, comprising the steps of: a, measuring a fluorescent emission in each micro-well of a dPCR chip before the start of a digital PCR ($F_s$); b, measuring a fluorescent emission in each micro-well of the dPCR chip at the end of the digital PCR ($F_e$); c, determining an emission ratio $T=F_e/F_s$ for each micro-well; d, using a threshold value for the emission ratio T to identify micro-wells with positive PCR amplifications; and e, calculating a percentage of positive PCR amplification as a result of the digital PCR.

In a digital PCR system, more than one reporter fluorescent dyes along with a passive fluorescent dye are usually employed to detect target generation. Emissions from reporter fluorescent dyes are directly correlated with PCR generation of nucleic acids while emission from the passive fluorescent dye is not related with PCR generation of nucleic acids. Measurement of both reporter fluorescent dyes and passive fluorescent dye are made before and after a digital PCR. $F_s$ is a fluorescent emission reading made before the start of the digital PCR. It can be an emission reading of a reporter fluorescent dye or a passive fluorescent dye. $F_e$ is a fluorescent emission reading made after the end of the digital PCR. It is an emission reading of a reporter fluorescent dye. Preferably, $F_e$ and $F_s$ are crosstalk calibrated emission readings. The ratio $F_e/F_s$ is used as a determinant to identify positive and negative amplifications by comparing to a threshold. The threshold ratio is selected as a value that is higher than the ratio of background level. The method for selecting a threshold in digital PCR analysis is well known to the one with ordinary skill in the art. For example, US20150269756A1 discloses a method of selecting a threshold for digital PCR analysis using a scatter plot or a histogram of fluorescent emission readings. When the ratio $F_e/F_s$ of a micro-well is higher than a threshold, the micro-well is considered to have a positive PCR amplification, that is, it contains a target nucleic acid sequence. When the ratio $F_e/F_s$ of a micro-well is smaller than a threshold, the micro-well is considered to have a negative PCR amplification, that is, it does not contain a target nucleic acid sequence. In some embodiments, $F_s$ and $F_e$ are measurements of the same reporter fluorescent dye. In other embodiments, $F_s$ is a measurement of a passive fluorescent dye and $F_e$ is a measurement of a reporter fluorescent dye. After micro-wells with positive amplifications are identified, the percentage of positive micro-wells can be calculated to be the result of the digital PCR.

Figure 9:
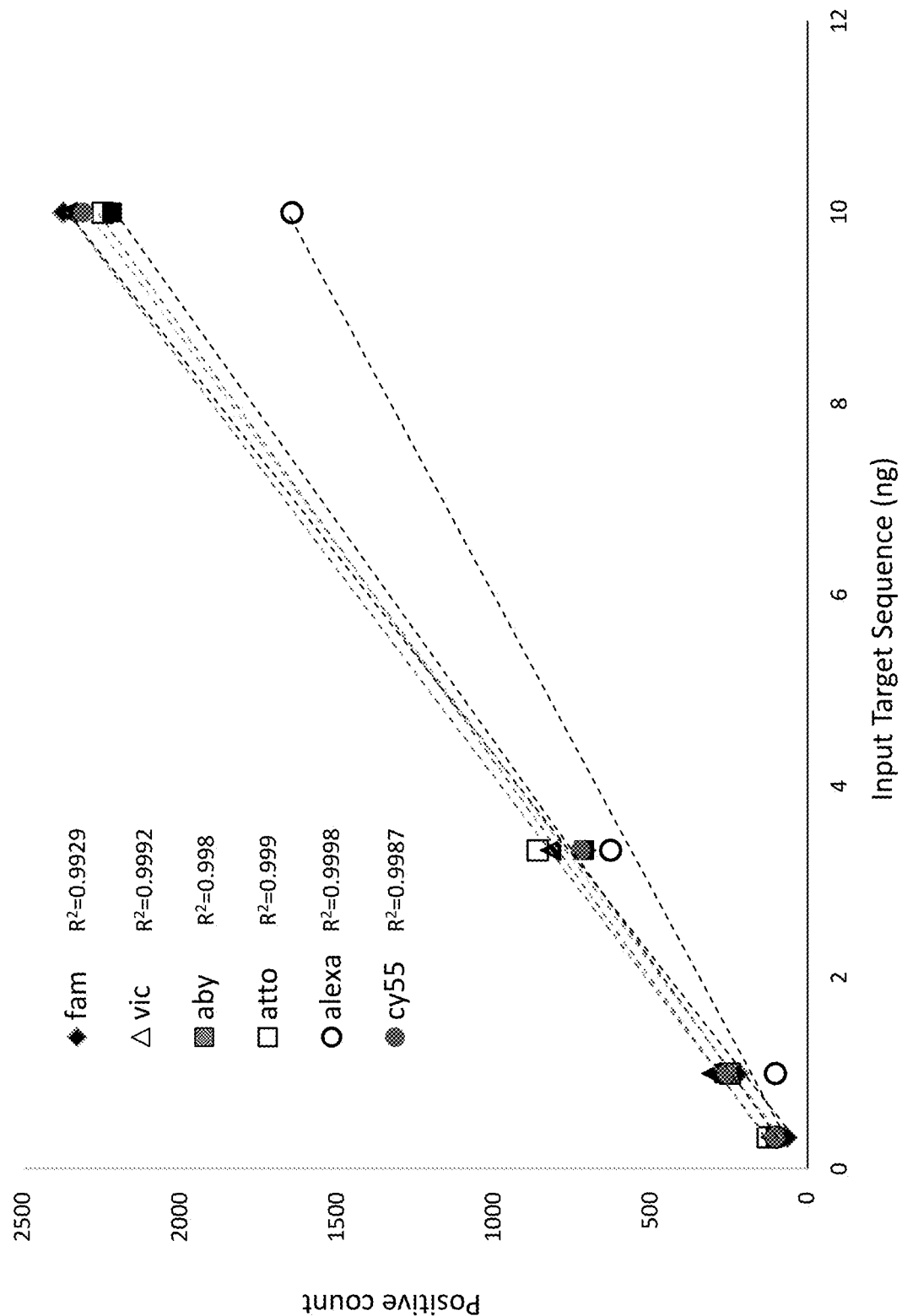
FIG. 9 shows a linearity analysis of a six-plex digital PCR experiment. Six different target sequences in a sample were detected in the digital PCR assay by six different fluorescent probes labeled by FAM, VIC, ATTO, ABY, ALEXA, or Cy5.5. The x-axis represents the positive count of target sequences determined by the digital PCR assay. The y-axis represents the amount of input target sequence added by serial dilution.

FIG. 9 shows a linearity analysis of a six-plex digital PCR experiment using six different fluorescent probes to detect six different target sequences in the same sample. All the six fluorescent probes (FAM, VIC, ATTO, Cy5.5, Alexa and Aby) showed good linearity with $R^2$ value higher than 0.99. The fluorescent emissions were read by the multicolor fluorescence reader of the invention and fluorescence data were calibrated for crosstalk using the methods described herein. The fluorescence reader successfully read emissions from seven fluorescent dyes in a sample, including six reporter fluorescent dyes and a passive fluorescent dye.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A multicolor fluorescence reader, comprising an emission filter wheel and two excitation channels that can be automatically moved, wherein each excitation channel has a light source, an excitation filter, and a dichroic mirror, wherein the multicolor fluorescence reader can read up to seven different fluorophores in a single run.

2. The multicolor fluorescence reader of claim 1, wherein the excitation channel is moved by a stepper motor.

3. The multicolor fluorescence reader of claim 1, wherein the emission filter wheel has three, four, five, six or more emission filters.

4. The multicolor fluorescence reader of claim 1, wherein the light source is selected from light-emitting diode (LED) lamps, xenon arc lamps and mercury-vapor lamps.

5. The multicolor fluorescence reader of claim 4, wherein the light source in a first excitation channel is a high-power LED lamp with a peak wavelength of <500 nm and the light source in a second excitation channel is a high-power LED lamp with a peak wavelength of >580 nm.

6. The multicolor fluorescence reader of claim 5, wherein the first excitation channel can be used to excite five different fluorophores and the second excitation channel can be used to excite two different fluorophores.

7. The multicolor fluorescence reader of claim 6, wherein the emission filter wheel has six emission filters.

8. The multicolor fluorescence reader of claim 6, wherein the multicolor fluorescence reader can measure emissions from seven fluorophores of FAM, VIC, ABY, JUN, Cy5, Cy5.5 and ATTO.

9. The multicolor fluorescence reader of claim 1 further comprises a slide holder that can hold multiple glass slides.

10. A multicolor fluorescence reader, comprising an emission filter wheel and two excitation channels that can be automatically moved, and a PCR chip holder that can hold multiple PCR chips, wherein each excitation channel has a light source, an excitation filter, and a dichroic mirror, wherein the multicolor fluorescence reader can read up to seven different fluorophores in a single run.

11. The multicolor fluorescence reader of claim 10, wherein the excitation channel is moved by a stepper motor.

12. The multicolor fluorescence reader of claim 10, wherein the emission filter wheel has three, four, five, six or more emission filters.

13. The multicolor fluorescence reader of claim 10, wherein the light source is selected from light-emitting diode (LED) lamps, xenon arc lamps and mercury-vapor lamps.

14. The multicolor fluorescence reader of claim 13, wherein the light source in a first excitation channel is a high-power LED lamp with a peak wavelength of <500 nm and the light source in a second excitation channel is a high-power LED lamp with a peak wavelength of >580 nm.

15. The multicolor fluorescence reader of claim 14, wherein the first excitation channel can be used to excite five different fluorophores and the second excitation channel can be used to excite two different fluorophores.

16. The multicolor fluorescence reader of claim 15, wherein the emission filter wheel has six emission filters.

17. The multicolor fluorescence reader of claim 15, wherein the multicolor fluorescence reader can measure emissions from seven fluorophores of FAM, VIC, ABY, JUN, Cy5, Cy5.5 and ATTO.

* * * * *